US012564347B2

(12) United States Patent
Clotworthy

(10) Patent No.: US 12,564,347 B2
(45) Date of Patent: Mar. 3, 2026

(54) DEVICE, SYSTEM AND METHOD FOR ACQUIRING AND MONITORING OF BIOMETRIC ELECTRICAL SIGNALS

(71) Applicant: B-SECUR LIMITED, Belfast (GB)

(72) Inventor: Christopher Clotworthy, Belfast (GB)

(73) Assignee: B-SECUR LIMITED, Belfast (GB)

( * ) Notice: Subject to any disclaimer, the term of this patent is extended or adjusted under 35 U.S.C. 154(b) by 779 days.

(21) Appl. No.: 17/772,118

(22) PCT Filed: Oct. 30, 2020

(86) PCT No.: PCT/GB2020/052741
§ 371 (c)(1),
(2) Date: Apr. 26, 2022

(87) PCT Pub. No.: WO2021/084261
PCT Pub. Date: May 6, 2021

(65) Prior Publication Data
US 2022/0378354 A1      Dec. 1, 2022

(30) Foreign Application Priority Data
Oct. 31, 2019      (GB) ...................................... 1915873

(51) Int. Cl.
*A61B 5/28*          (2021.01)
*A61B 5/0531*          (2021.01)

(52) U.S. Cl.
CPC .............. *A61B 5/28* (2021.01); *A61B 5/0531* (2013.01)

(58) Field of Classification Search
CPC ......... A61B 5/28; A61B 5/0531; G06V 40/10
See application file for complete search history.

(56) References Cited

U.S. PATENT DOCUMENTS

| | | | |
|---|---|---|---|
| 2011/0068632 A1* | 3/2011 | Du | H02J 4/00 307/80 |
| 2012/0065536 A1* | 3/2012 | Causevic | A61B 5/30 600/544 |

(Continued)

FOREIGN PATENT DOCUMENTS

| | | | | |
|---|---|---|---|---|
| CN | 108663596 A | * 10/2018 | ............. | G01R 31/66 |
| GB | 2 534 280 A | 7/2016 | | |

(Continued)

OTHER PUBLICATIONS

International Search Report and Written Opinion for International Application No. PCT/GB2020/052741, dated Dec. 18, 2020 (11 pages).

(Continued)

*Primary Examiner* — Linda C Dvorak
*Assistant Examiner* — William Mossbrook
(74) *Attorney, Agent, or Firm* — Foley & Lardner LLP

(57)          ABSTRACT

There is provided a device for acquiring biometric electrical signals comprising at least two electrodes. The device also comprises a current supply comprising a direct current supply, an alternating current supply, and a switch actuatable to switch selectively between the direct current supply and the alternating current supply. The device further comprises a capacitive coupling to couple each electrode to the current supply, a direct coupling to couple each electrode to the current supply, and a switch actuatable to switch selectively between the direct coupling and the capacitive coupling. The device also comprises a data acquisition module.

16 Claims, 12 Drawing Sheets

100

150

101

152          153

151

(56) References Cited

U.S. PATENT DOCUMENTS

2016/0331257 A1*  11/2016  Baumann ............... G16H 40/67
2016/0374577 A1    12/2016  Baxi et al.
2020/0403828 A1*  12/2020  Reddy ............... H03K 17/6872

FOREIGN PATENT DOCUMENTS

GB          2 570 535 A     7/2019
WO      WO-03/008039 A1     1/2003

OTHER PUBLICATIONS

Search Report for great britian Application No. 1915873.2, dated May 18, 2020 (3 pages).
Examination Report Office Action on International Application No. 20 801 374.8-1113 dated Jun. 25, 2024 (2 Pages).
Examination Report Office Action on International Application No. 20 801 374.8-1113 dated Sep. 10, 2024 (2 Pages).
International Preliminary Report on Patentability on PCT/GB2020/0527415 dated May 12, 2022 (9 pages).
CN First Office Action for Application No. 202080086801.8 mailing date Jan. 18, 2025, 8 pages.

* cited by examiner

150

100

400

1

DEVICE, SYSTEM AND METHOD FOR ACQUIRING AND MONITORING OF BIOMETRIC ELECTRICAL SIGNALS

CROSS-REFERENCE TO RELATED APPLICATIONS

This application is a U.S. National Phase Application of International Application No. PCT/GB2020/052741, filed Oct. 30, 2020, which claims the benefit of Great Britain Patent Application 1915873.2, filed Oct. 31, 2019, which are hereby incorporated by reference in their entirety.

FIELD OF DISCLOSURE

This invention relates to a device, system and method for acquiring and monitoring of biometric electrical signals, such as electrocardiogram a skin contact device, such as a wearable.

BACKGROUND

Wearable and touch technology is becoming more evident and widely available on the world market, with increasing technologies and products being adapted into wearables and touch sensitive devices. One particular technological area of increasing interest is in the acquisition of biometric information through biometric sensing. Obtaining this information allows technology to enhance further as it can be implemented into a range of functional applications such as improved security, personalised authentication, personal health monitoring and stress detection, to name a few.

The acquiring and monitoring of biometric electrical signals may be of value in its own right, for example as a mean of monitoring underlying physiological conditions or processes. Additionally, it may have value as a form of biometric sensing for other purposes such as for identification/authentication. Biometric sensing may be superior over other more common forms of personal physical detection, such as fingerprint recognition, iris response and voice activation. It is particularly favourable in security and authentication systems, as it is more difficult to replicate an individual's natural characteristics, such as their heartbeat, muscle activity and sweat gland response.

The ability to sense characteristic biometric information associated with an individual's heartbeat may be of particular interest in this regard. The electrical signals from the heart provide a trace of data points which are unique to each individual and cannot be replicated, even when the heart is subjected to different stresses, i.e. when an individual exercises.

The most common way to measure a subject's heartbeat is to measure the electrical signals using an electrocardiogramhich records the electric potential changes in the heart over time. A longer recording of such electrical activity is known as an electrocardiogram or ECG. This ECG measurement is recorded using a pair (or more) of electrodes which measure the changes in electric potential between the points of contact of the electrodes. In clinical situations the ECG electrodes make contact with a subject's skin by predominantly using adhesive gelled electrodes, and are positioned at various points across the heart in order to achieve an accurate reading. The change in electric potential is strongly correlated with heart and muscle activity as the heartbeat of an individual is stimulated through electrical impulses. The basic elements of a single heart beat are: a P wave generated when the right and left atria of the heart are depolarized; a QRS complex reflecting the depolarization of the right and left ventricles; and a T wave corresponding to the ventricular repolarization. Existing methodologies attempt to characterise an individual by these different elements and their respective sizes, shapes and positions.

Biometric electrical signals associated with an individual's heartbeat may be particularly characteristic of an individual, and examples are discussed herein in which such characteristic biometric electrical signals are acquired and monitored. However, the skilled person will not infer by such examples that the invention need be limited to any particular class of biometric signal characteristic of any particular physiological activity, but will understand that any biometric signal capable of characterising an individual may find application in the context of the invention.

A useful means for acquiring and monitoring of biometric electrical signals from a subject is a skin contact device, such as a wearable. Many biometric sensing devices have been adapted to measure the natural characteristics of a user while also being small enough to be enabled as a wearable device or affixed in other contact-type devices. However, several issues still arise when seeking to acquire biometric electrical signals from a subject using a skin contact device, such as a wearable, particularly where the use of the device is intended in day-to-day application in non-clinical environments.

Such issues may be considered for example by looking at the problems that might arise when measuring an individual's ECG through a wearable or contact device. The clinical method of measuring ECG is not suitable in such day-to-day application in non-clinical environments. For example, with contact devices for domestic application and/or for use in or comprising part of consumer products, such as smart watches, wearable bands, steering wheels, joysticks, etc. These applications typically require the use of dry electrodes and are often limited to using only two electrodes, due to limited space on small sized consumer products, however if the product is not space limited a larger plurality of electrodes may be used. In addition, the amplifiers used in clinical devices such as clinical ECGs exhibit high voltage rails which allow for greater offset potentials to be tolerated. This is impractical for small battery-operated equipment such as smart watches, or other wearable consumer devices.

Similar problems can be anticipated in relation to the use of a skin contact device, such as a wearable, when seeking to acquire various other biometric electrical signals from a subject where the skin contact device is intended in day-to-day application in non-clinical environments, and for example in domestic applications or for use in consumer products, such as smart watches, wearable bands, steering wheels, joysticks, etc.

Most dry electrodes are made from noble metal materials, such as silver, gold, copper, etc, as they have little or no polarisation effects when in contact with skin, reducing the offset potential at the skin/electrode junction. Other highly capacitive materials can be used but produce suboptimal data acquisition performance due to the high polarisation effects at the skin/electrode junction when a DC current passes through the electrode system. This current is required in order to detect when the user makes contact with the electrodes. These materials may be chosen to satisfy aesthetic requirements of the consumer product, such as the need for coloured or textured finishes. To overcome the large and unstable potential offset of these conducting materials alternative methods of operation using AC-coupling to the electrodes are known. The AC-coupling necessitates the use of AC current for lead on and off detection; however this requires more power as the method is much more complex than that using DC current.

Power drain is likely to be a much more critical factor in relation to a device which is intended in day-to-day domestic applications or for use in consumer products, such as smart watches, wearable bands, steering wheels, joysticks, etc. Such a device may be actively acquiring data only intermittently and spend long periods idle waiting for a skin to electrode contact to be made. The effect may be greatest where the power source is a compact battery. The use of AC current for lead on detection in such cases would therefore necessitate much higher battery drain and is likely to be of limited practicability in many such devices.

Therefore, there is a need to reduce power consumption and in particular battery power consumption in wearable and/or portable devices while maintaining a low differential potential offset at the amplifier input, in order to utilise a wider range of conducting materials.

The invention is directed at the provision of a device, system and method for acquiring and monitoring of biometric electrical signals from an individual subject, and in particular of biometric electrical signals tending to be characteristic of the subject.

The invention is in particular directed at the provision of a skin contact device, such as a wearable, and to a system and method incorporating the same, for acquiring and monitoring of biometric electrical signals in non-clinical domestic environments.

The invention is directed at the provision of a device, system and method that facilitates the use of alternative electrode materials as electrodes for dry skin contact in intended use.

SUMMARY OF INVENTION

In one aspect of the invention, there is provided a device for acquiring biometric electrical signals, comprising:

at least two electrodes;

a current supply comprising a direct current supply, an alternating current supply, and a switch actuatable to switch selectively between the direct current supply and the alternating current supply;

a capacitive coupling to couple each electrode to the current supply, a direct coupling to couple each electrode to the current supply, and a switch actuatable to switch selectively between the direct coupling and the capacitive coupling;

a data acquisition module.

The electrodes are applied in use to, and are adapted to be so applied in use to, spaced locations on the skin surface of the body of a living animal, and in particular on the skin surface of the body of a human subject. The electrodes are thus able to apply a potential difference to the skin at the spaced locations to detect contact between the electrodes and skin, and transmit the resultant mediated biopotential signals from the skin surface to the biometric data acquisition module, so that biometric electrical data associated with one or more physiological processes can be acquired thereby and one or more such physiological processes can be monitored thereby.

To that extent, the device of the first aspect of the invention is a conventional skin contact device, which can for example be configured as a wearable, by means of which biometric electrical signals from remotely spaced skin contact points may be acquired from and/or monitored in a subject.

It is characterised by the provision of a selectively switchable DC or AC current supply and by being switchable between a switchable direct connection and a capacitive coupling electronically coupling each electrode to the current supply and to the data acquisition 5 module. The device is thus configured to have two modes of operation.

In a first mode of operation, the DC current supply and the DC connection are selected, a direct current is supplied to each electrode and a direct electrical connection is made between the electrode and the data acquisition module in generally conventional manner. In the second mode of operation, the AC current supply and the capacitive coupling are selected and an alternating current is supplied to each electrode. The frequency of this AC current supply is designed to be much higher than the content of the signal being measured, so that lead on/off detection can be carried out simultaneously with biopotential signal data acquisition.

The device is conveniently configured to be switchable between the said first mode of operation, wherein the DC current supply and the DC connection are selected, a direct current is supplied to each electrode and a direct electrical connection is made between the electrode and the data acquisition module; and the said second mode of operation, wherein the AC current supply and the capacitive coupling are selected and an alternating current is supplied to each electrode.

In an intended use, where the device is intended for intermittent/occasional periods of data acquisition based on intermittent/occasional periods of skin contact, with periods of idleness between, the first mode of operation may be utilised as an idle mode, for example for operation when the electrodes are not in contact with the skin of a subject and the circuit constituted by the electrodes is open, and the second mode of operation may be utilised as an active mode, for example for operation when the electrodes are in contact with the skin of a subject and the circuit constituted by the electrodes is thereby closed and data is intended to be actively acquired.

This provides the advantages of AC-coupled data acquisition during the active mode phase of use, in particular overcoming the potential offset at the skin/electrode junction, in order to utilise a wider range of conducting materials, while reducing power consumption in the idle phase of use waiting for a skin to electrode contact to be made, to reduce overall power consumption and in particular battery power consumption which is likely to be of particular value in wearable and/or portable devices and/or devices for domestic use.

In some embodiments, the device further comprises a battery power source as a source of electrical power for the AC current supply and the DC current supply. Additionally, or alternatively, other integral or remote sources of electrical power may be provided.

The electrodes may be adapted for use as dry electrodes, that is making direct contact with the skin in use without requirement for any electrolyte gel or the like. The electrodes may nevertheless be fabricated from materials that create potentially large and/or unstable potential offsets at the skin/electrode junction but that might be otherwise desirable for aesthetic requirements in a consumer product, such as the need for coloured or textured finishes, as the AC acquisition mode mitigates the limitations of such materials.

For example, the electrodes may be fabricated from materials including surface layers such as passivating layers that may tend to create capacitive offsets at the skin/electrode junction in use, including but not limited to:

Chromium-plated metal or plastic;

Coloured/colourable nitrides or coloured/colourable nitride coatings, in particular titanium nitride, for example applied by physical vapour deposition (PVD) methods;

stainless steels, especially with passivating coatings.

In convenient embodiments, the device may be adapted to switch between the first, or idle mode of operation, and the second, or active mode of operation, automatically when contact is made between electrodes and skin. Such contact closes the circuit between the electrodes. The device may comprise a closed circuit detection module to detect closure of the circuit between the electrodes when contact is made between electrodes and skin and a switching module to effect switching between the first mode of operation and the second mode of operation when such contact is made.

Additionally, or alternatively, the device may be adapted to switch between the first, or idle mode of operation, and the second, or active mode of operation, at the instigation of a user. A user actuatable mode switch may be provided.

In some embodiments, each electrode may be provided with a capacitive coupling to couple each electrode to the current supply, and a direct coupling in parallel to the capacitive coupling provided with a selectively closable switch. With the switch associated with the direct coupling closed, the capacitive coupling is shorted, and a direct electrical connection is made to the electrode in generally conventional manner. With the switch open, the direct electrical connection is no longer made but instead the electrode connects via the capacitive coupling. The switch thus serves to switch the electrode selectively between the direct coupling and the capacitive coupling.

In some embodiments the capacitive coupling may comprise an AC-coupling capacitor.

In some embodiments a discrete DC source and a discrete AC source are provided, and a switch selectively switches between the DC source and the AC source.

In some embodiments, the switch further comprises a mid-rail bias point, whereby the DC source and the AC source can be selectively switched in and out of the circuit via the mid-rail bias point.

The device may further comprise one or more of: a data storage module to store acquired data and/or library data against which acquired data may be compared for identification of a subject; a data comparator module to compare acquired data to stored library data, for example including older template signal traces, against which acquired data may be compared for example for identification identification/authentication purposes, or for longer term biometric signal monitoring.

The device may further comprise a data transmission module to transmit data to a remote recipient to enable further processing. For example, the device may be adapted for a suitable mode of wireless communication via a WLAN protocol.

In another aspect of the invention, there is provided a system for acquiring biometric electrical signals, comprising: a device in accordance with the first aspect of the invention, an additional receiving device, a wireless communication system operable to effect communication of data between the device and the additional receiving device, a data storage module comprising a part of the device and/or the additional receiving device.

Optionally, the data storage comprises stored library data for example including older template signal traces for example for identification/authentication purposes. Optionally, the system further comprises a data comparator module to compare acquired data to stored library data, for example including older template signal traces, against which acquired data may be compared for example for identification identification/authentication purposes, or for longer term biometric signal monitoring.

In another aspect of the invention, there is provided a method for acquiring biometric electrical signals comprising:

providing a device having:

at least two electrodes;

a current supply comprising a direct current supply, and an alternating current supply;

a capacitive coupling to couple each electrode to the current supply and a direct coupling to couple each electrode to the current supply;

whereby the device is selectively switchable between:

a first mode of operation, wherein the DC current supply and the DC connection are selected, and a direct current is supplied to each electrode;

and a second mode of operation, wherein the AC current supply and the capacitive coupling are selected and an alternating current is supplied to each electrode;

operating the device in the first mode when the electrodes are not in contact with a subject;

operating the device in the second mode when the electrodes are in contact with the skin surface of the body of a subject.

Thus, the first mode of operation may be utilised as an idle mode, and the second mode of operation may be utilised as an active mode, during which data is actively acquired. This provides the advantages of AC data acquisition during the active mode but reducing power consumption in the idle mode as above described.

In some embodiments the method further comprises the switching of the device between the first mode of operation and the second mode of operation via a mid-rail or ground.

In some embodiments the method further comprises comparing the acquired data to other data for example library data comprising older template signal traces, which can be used for identification/authentication or for longer term biometric monitoring.

In some embodiments the method further comprises transmitting the acquired data to a remote recipient via wireless communication, following the acquisition of such data, for further processing.

The invention in this aspect is for example a method of use of the device of the first aspect or the system of the second aspect, and further preferred features of the method will be understood by analogy with the discussion of those aspects.

DETAILED DESCRIPTION

Figure 1B:
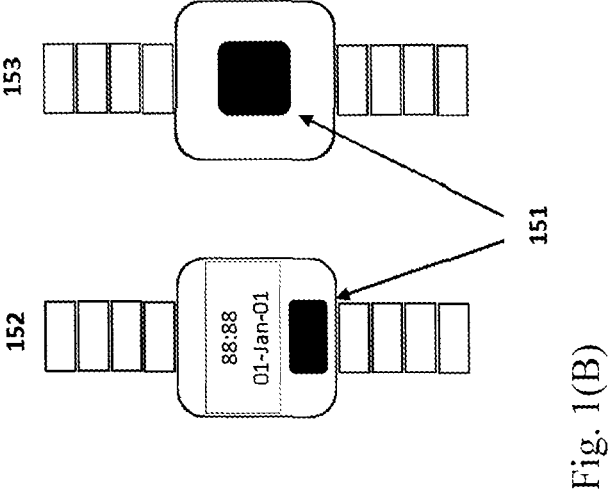
FIG. 1(B) depicts a 2-electrode ECG acquisition application of a smart watch where the electrodes are positioned on the front and rear of the watch.
Figure 1A:
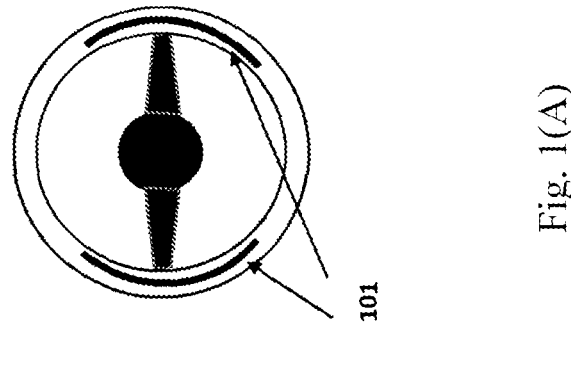
FIG. 1(A) depicts a 2-electrode ECG acquisition application of a steering wheel where the electrodes are positioned for right and left hand contact.

FIG. 1 provides example applications of a 2-electrode ECG detection and acquisition device as described throughout this document as a preferred embodiment. FIG. 1 illustrates that the device can be implemented in consumer products, for example, but not limited to, (A) a steering wheel 100 and (B) a smart watch 150. The electrodes 101 in FIG. 1(A) are positioned on either side of the steering wheel, i.e. separately spaced locations, to enable 2-point skin contact, namely a user's left and right hand side. The electrodes 101 are also constructed and shaped to cover a large portion of the left and right sides of the steering wheel providing an increased contact area. Similarly, the electrodes 151 in FIG. 1(B) are positioned in spaced locations in order to enable 2-point skin contact, that being the front 152 and rear 153 faces of the smart watch 150. This enables a wrist contact with one electrode and an opposing finger contact with the other electrode. Again, the electrodes 151 are constructed and shaped to fit on either side of the smart watch while providing accessible contact areas. Electrodes can be constructed in various shapes and sizes to fit the consumer product, with each electrode having its own shape and size if necessary, such as illustrated by the different sized front and rear electrodes in FIG. 1(B).

The embodiments are discussed by way of example with reference to obtaining biometric electrical signals associated with an individual's heartbeat, and in particular ECG traces. Such traces are of course valuable in their own right as an indicator of cardiovascular physiology, but may also be particularly characteristic of an individual. Of course, the same principles could be applied to any biometric signal capable of characterising an individual and/or providing an indicator of a physiological condition or process.

ECG acquisition can be performed when a user has made contact with both 2 electrodes, measuring the signal across the electrodes via the user. In relation to the steering wheel 100 the measurement can be taken when both hands are in contact with the electrodes 101 on either side of the wheel, and for the smart watch 150 the acquisition can be made when the wrist is in contact with the rear electrode and a finger makes contact with the front electrode. Other configurations may be apparent depending on the placement of the electrodes in the receiving product.

Figure 2:
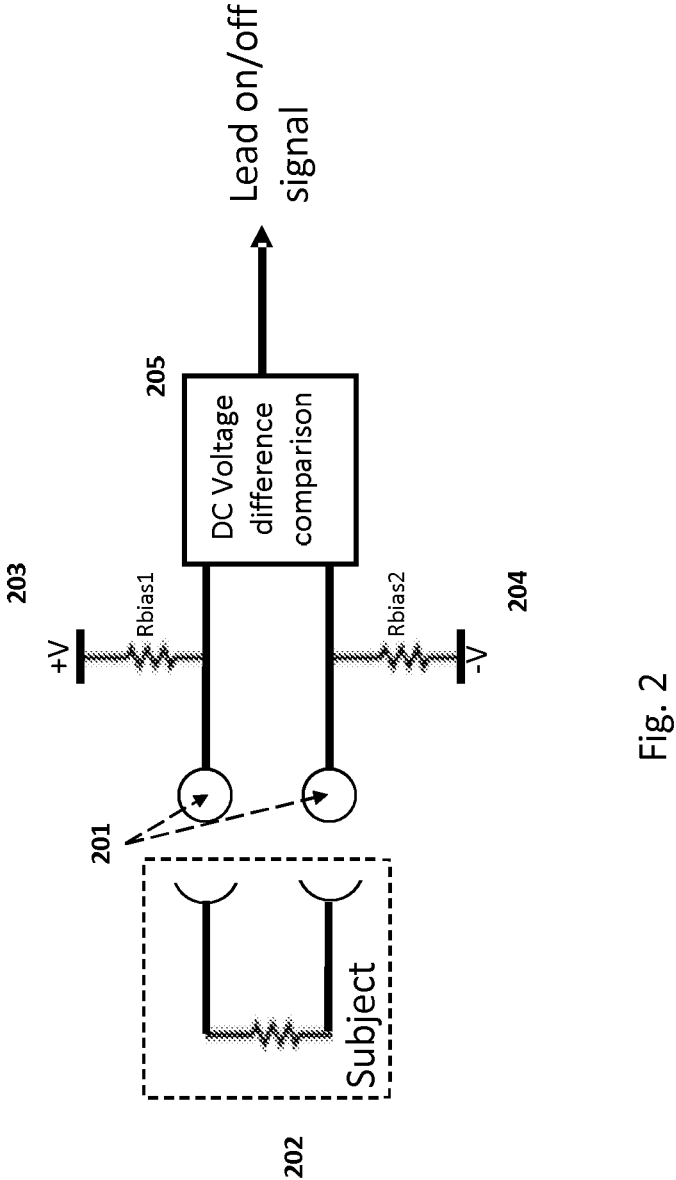
FIG. 2 shows a simple circuit diagram of DC lead-on/off detection mode where the electrodes detect that contact by a subject is made across the 2 electrodes, i.e. the DC voltage across the electrodes is high.

FIG. 2 depicts a typical circuit for contact detection 200 used to detect when a subject or user makes contact with the device, which is often referred to as lead-on detection, and lead-off when contact between skin and electrodes is broken. FIG. 2 illustrates the electrodes 201 at the open end of the circuit in idle or "sleep" mode, awaiting contact from a subject or user 202. Common biometric contact detection circuits feed a direct current (DC) current into one electrode, usually positive 203, and out of the other, usually negative 204, and measures the voltage difference between the 2 electrodes. This voltage difference will be compared to an established threshold value, i.e. an open circuit voltage such as Vemf. Usually for human subjects if the corresponding resistance is less than a typical resistance threshold of approximately 5 MΩ the subject is considered to be connected to the electrodes. Once a connection is made and contact has been detected the ECG acquisition can begin. Typically, this is carried out using a low-power voltage comparator 205. The lead detection can be continued through the signal acquisition for determining lead-off, i.e. when the subject breaks contact from the electrodes. However, there are limitations in the material choice for the dry electrodes used within a DC circuit, due to polarization effects at the skin/electrode interface. Some materials with thin leaky dielectric layers give rise to large polarisation effects, producing a large voltage offset potential. This can make it difficult to detect and acquire the ECG signal over the threshold of the circuit electronics. The imposed voltage offset of these materials is in addition to the electrochemical half-cell potential produced at the boundary between the ions in the subject's body and the electrode itself. The DC offset can also vary between the 2 electrodes according to skin site, pressure, area or if two different materials are used for each electrode. The difference in voltage between the electrodes can be more than 0.5V in some cases. The offset also varies across different people, due to the effect of differing skin impedance. Therefore, altering the combination of electrode material and electronics may not produce a valid ECG signal for a significant proportion of the population, limiting the choice of electrode material and finish.

Figure 3:
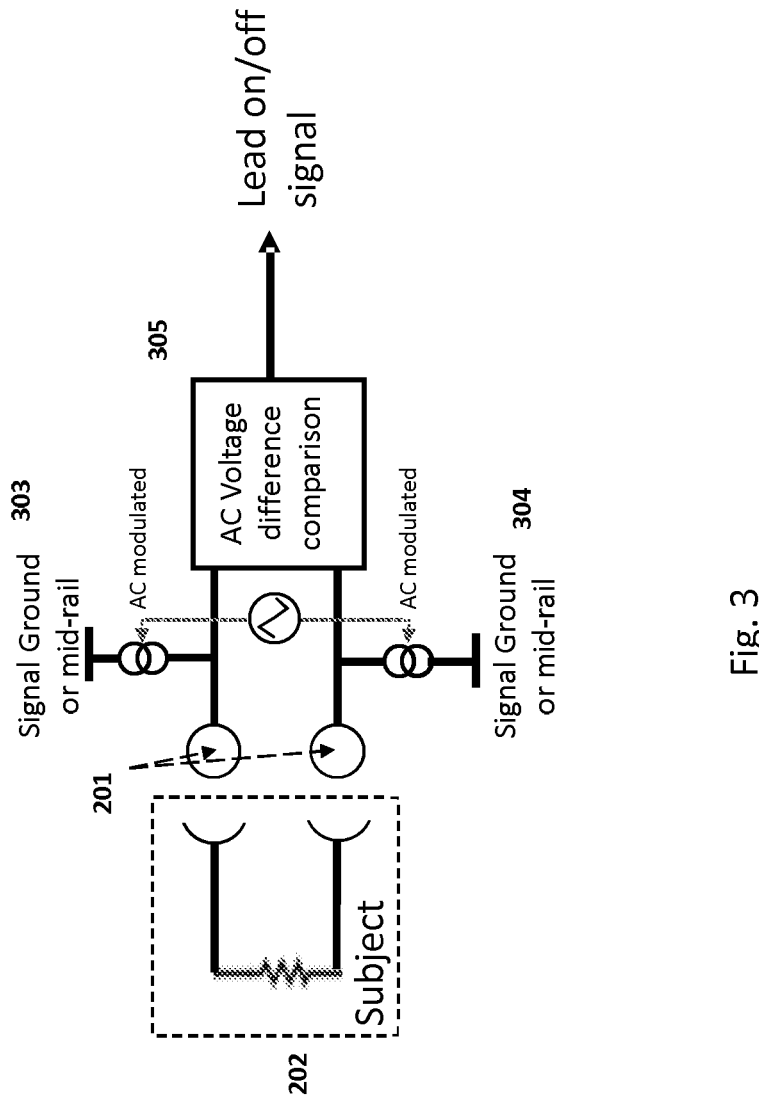
FIG. 3 shows a simple circuit diagram of AC lead-on/off detection mode where the electrodes detect that contact by a subject is made across the 2 electrodes, i.e. the AC voltage across the electrodes is high

Alternatively, the circuit for contact detection can have an alternating current (AC) feed rather than DC as depicted in FIG. 3. The electrodes 201 and subject 202 can be the same as for DC current, but instead a modulated AC current 303/304 is passed across the electrodes. It is necessary to operate the modulated AC current at a value higher than the required ECG bandwidth in order for detection and acquisition to occur. This overcomes the issues that arise with the DC circuit but requires more power. Again, like with the DC circuit, the AC circuit has a corresponding voltage comparator 305 to measure the difference in AC voltage for acquiring the ECG signal of the subject, and lead on/off detection can also be continued. However, as the AC driven circuit requires more power than DC small wearable devices have a greatly reduced available battery life.

A high-pass filter can be introduced in the DC circuit to combat the effects of polarisation, when using highly conductive materials with thin leaky dielectric layers for dry electrodes, by bringing the signal into a suitable displayed range of the device. High-pass filters can also account for a differentiating DC offset induced by different materials and different users. The value of the induced offset can be as much as 0.5 V, or more, for consumer devices when dry electrodes are used. The high-pass filter for consumer devices typically has a −3 dB roll-off value of 0.5 Hz. Typical values for clinical use ECG devices is normally around 0.05 Hz due to the use of adhesive gelled electrodes.

Figure 4:
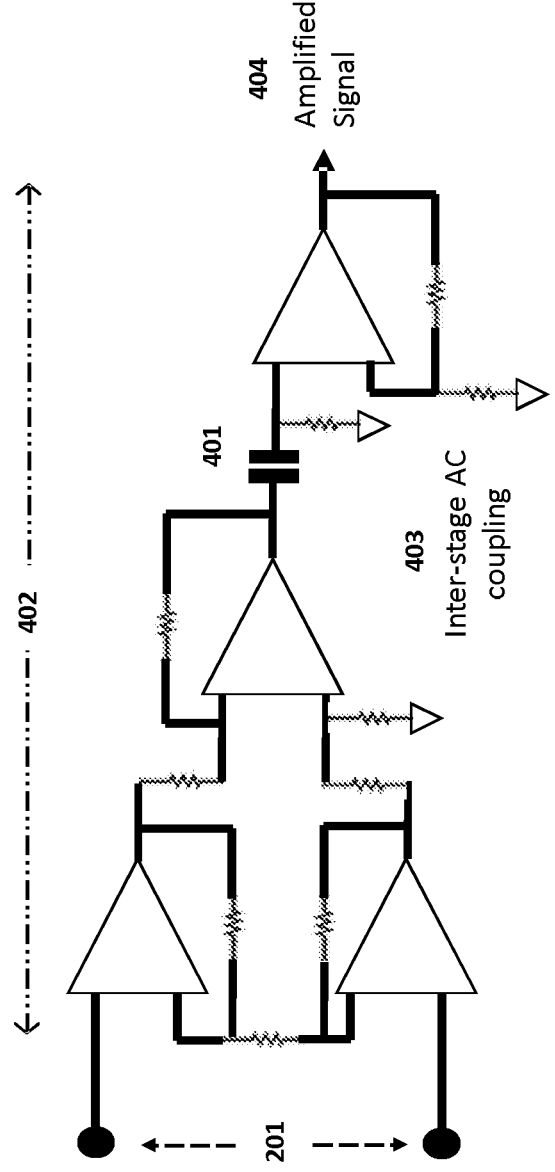
FIG. 4 shows a simple circuit diagram of an amplifier inter-stage AC coupling wherein the capacitor is coupled to the different stages of amplification.
Figure 5:
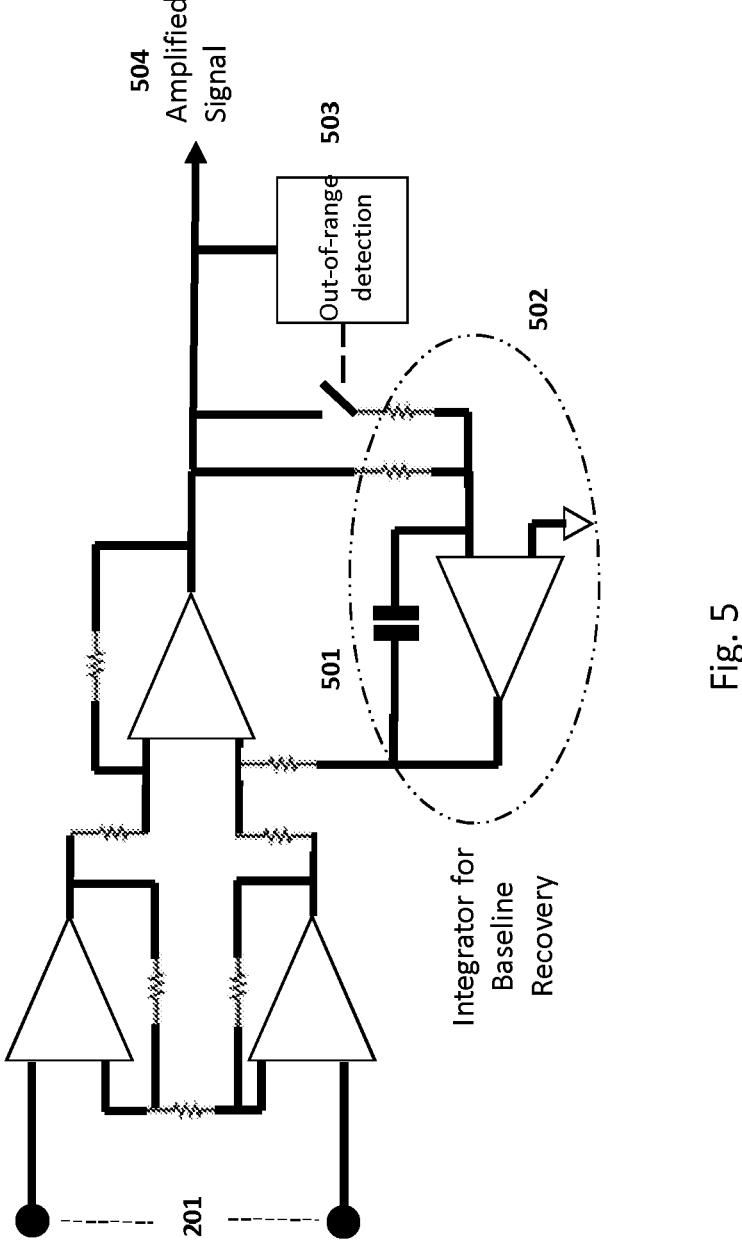
FIG. 5 shows a simple circuit diagram of an integrator in a feedback path for baseline recovery at the amplification stage.

The high-pass filter is able to pass the signal that has a higher frequency than a certain cut-off frequency, such as the value of the induced offset, and attenuates any signal that has a lower frequency than the cut-off frequency. This can be achieved using different circuit designs. For example, the high-pass filter can be implemented using a capacitor 401 as shown in FIG. 4, or by an integrator in a feedback path 501 as shown in FIG. 5. Other high-pass filter designs may also be adopted. The capacitor 401 introduced in the circuit 400 of FIG. 4 is coupled to the different stages of amplification 402 through inter-stage AC coupling 403 to remove the DC offset and provide an adjusted amplified signal 404 at the output. FIG. 5 shows the integrator 501 in the feedback path 502 of the circuit 500 for baseline recovery to account for the offset. The example in FIG. 5 also includes an optional fast baseline recovery 503 by detecting any out of range signals. This detects where the amplifier output has saturated, and reduces the integrator time constant until the average signal level is within the viable acquisition range, providing a quicker amplified signal 504 at the output. This is disclosed in U.S. Pat. No. 4,319,197.

However, these types of DC circuit modifications can also present problems. The inclusion of high-pass filters, such as the capacitor 400 and integrator 500 designs presented, suffer from limited offset potential capability due to the saturation of one or more of the amplification stages. This is especially problematic in the case of small wearable devices where the device is battery operated. This is especially limiting as the typical battery operated electronics for these types of devices operate with a low supply rail voltage, which is typically 1.8 V.

Figure 6:
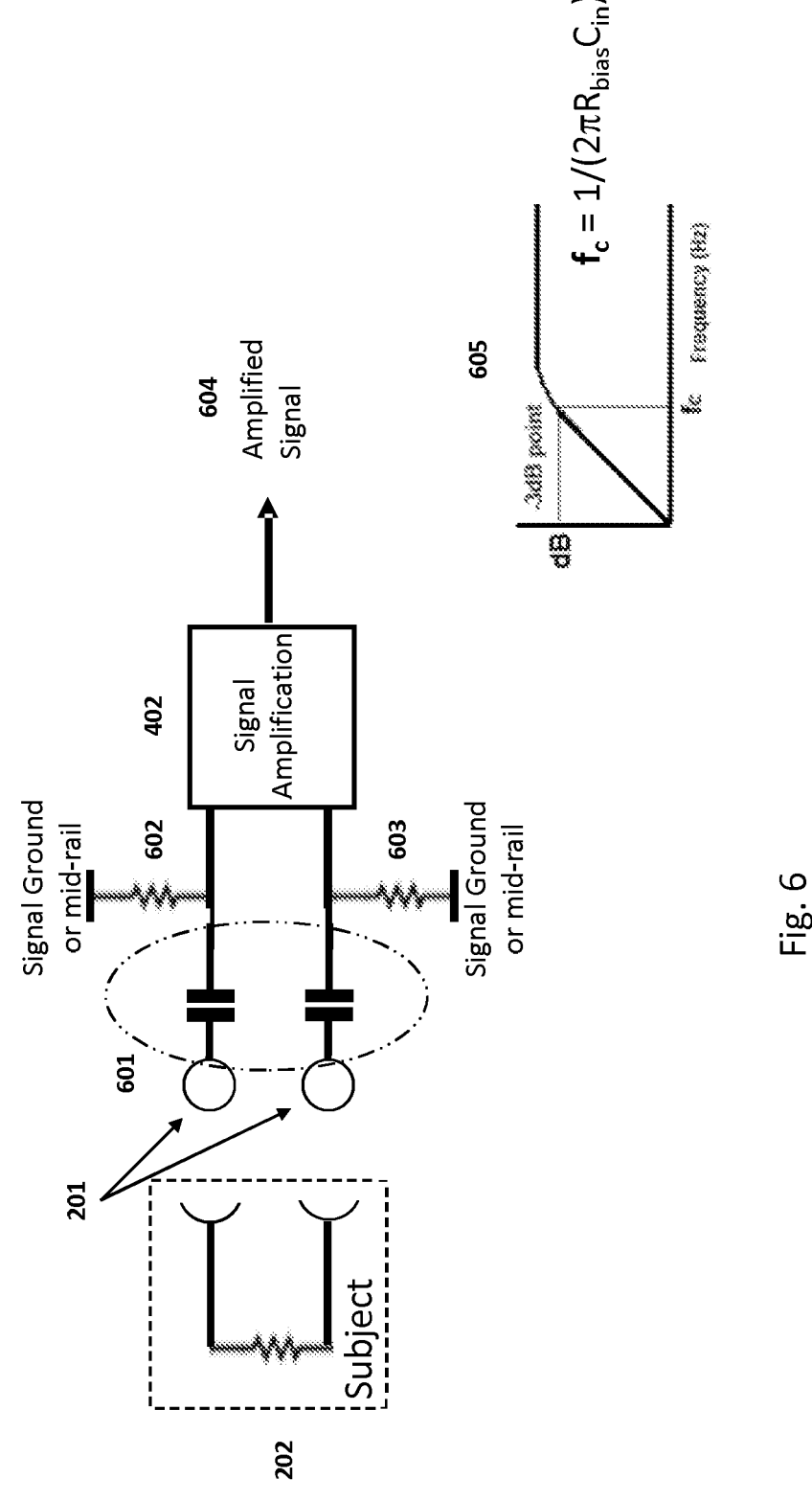
FIG. 6 shows a simple circuit diagram of AC coupling of electrodes to the amplifier inputs.

A further example to improve the ECG acquisition following lead-on detection is to AC couple both electrode inputs as shown in FIG. 6. This circuit design 600 offers improved biopotential signal processing for ECG acquisition as the AC coupling 601 is performed at the front-end of the circuitry instead of the inter-stages of the amplification 402 as shown by the capacitor 401 in FIG. 4. The AC coupled capacitors 601 and input bias resistors 602/603 at the front-end act as a balanced high-pass filter, removing the induced offset potential. However, this example is costly in order to achieve the required balanced high-pass filter. It requires expensive close-tolerance components to main a good common-mode rejection ratio (CMRR) at 50 or 60 Hz, which is needed for removing the effects of mains interference and avoiding low-frequency phase distortion in the acquired waveform ECG signal. Also, as the AC coupling 601 exists at the front end DC contact detection cannot be used. Therefore, AC current is required to pass through the capacitors during the inactive idle mode to detect a lead-on event (where the subject contacts both active electrodes), which as indicated above uses more battery power as it requires an increased current consumption during this mode.

Figure 7:
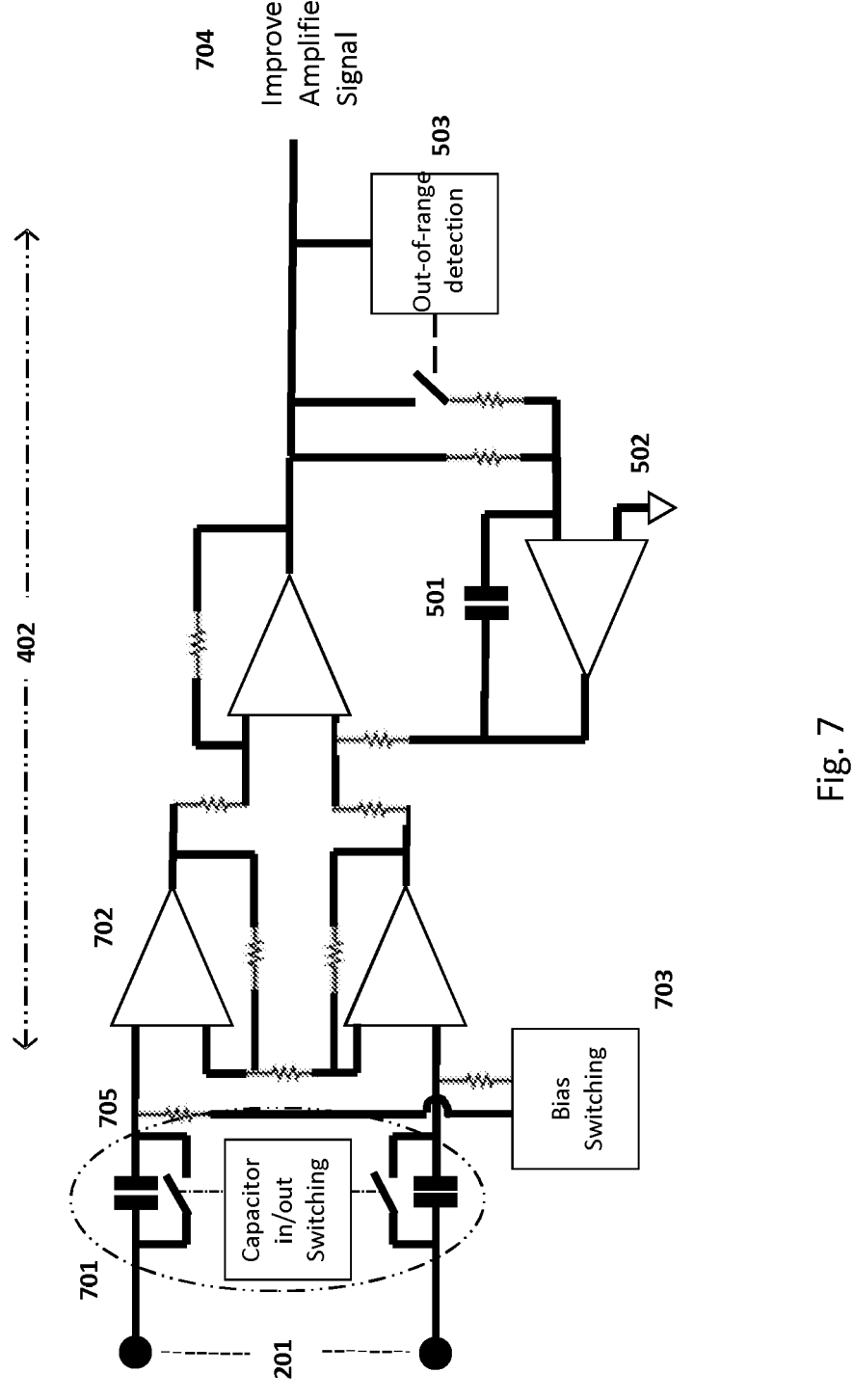
FIG. 7 is a circuit diagram of an ECG amplifier circuit wherein the AC-coupling capacitors can be switched in and out of the circuit.

In the preferred embodiment of FIG. 7, the biometric sensing device includes an electronic integrated circuit 700 implemented to acquire biometric electrical signals, the acquired biometric signals being at least one of electrocardiogram (ECG), electrodermal activity (EDA), electroencephalograph (EEG) or electromyograph (EMG) signal. It will be realised that the device may be adapted to measure other biometric signals. For this embodiment the signal being detected and acquired is ECG. The circuit 700 of the ECG sensing device includes 2 dry electrodes 201 to make contact between the device and a subject or user 202. The electrodes 201 convert ionic current within the body into electrical current. The electrodes 201 may comprise of one or more conducting or semiconducting materials, including those with a thin leaky dielectric layer that can be susceptible to polarisation effects. This allows a greater choice of materials and combinations of materials to be used for the dry electrodes, which can have other desirable properties such as varied colour options, or varied textured options, etc, providing enhanced aesthetics when incorporating in a consumer product. These include but are not limited to chromium-plated metals or plastics, coloured nitride coatings applied by PVD methods, stainless steels including stainless steels with passivating coatings, etc.

In a preferred embodiment, the circuit 700 includes AC coupled inputs 701, coupling the electrodes 201 to the amplifier 702 electronics. The amplifier 702 may be a differential instrumentation amplifier but other amplifiers may be apparent. The input AC coupling 701 prevents any mean DC current flowing through the electrode/skin interface 201, overcoming the potential offset that arises at such interface for highly polarising materials. This includes the current that is necessary to bias the amplifier 702 inputs to keep the amplifier electronics operating in a linear mode. The AC coupling also prevents the DC current which is induced in the circuit from possible motion artefacts or disturbances of the ECG baseline signal by movement, such as emf current. As the option to implement the device in a smart watch or other portable wearable is of great importance, there is a requirement to suppress or eliminate these currents from the output signal.

Figures 8A, 8B:
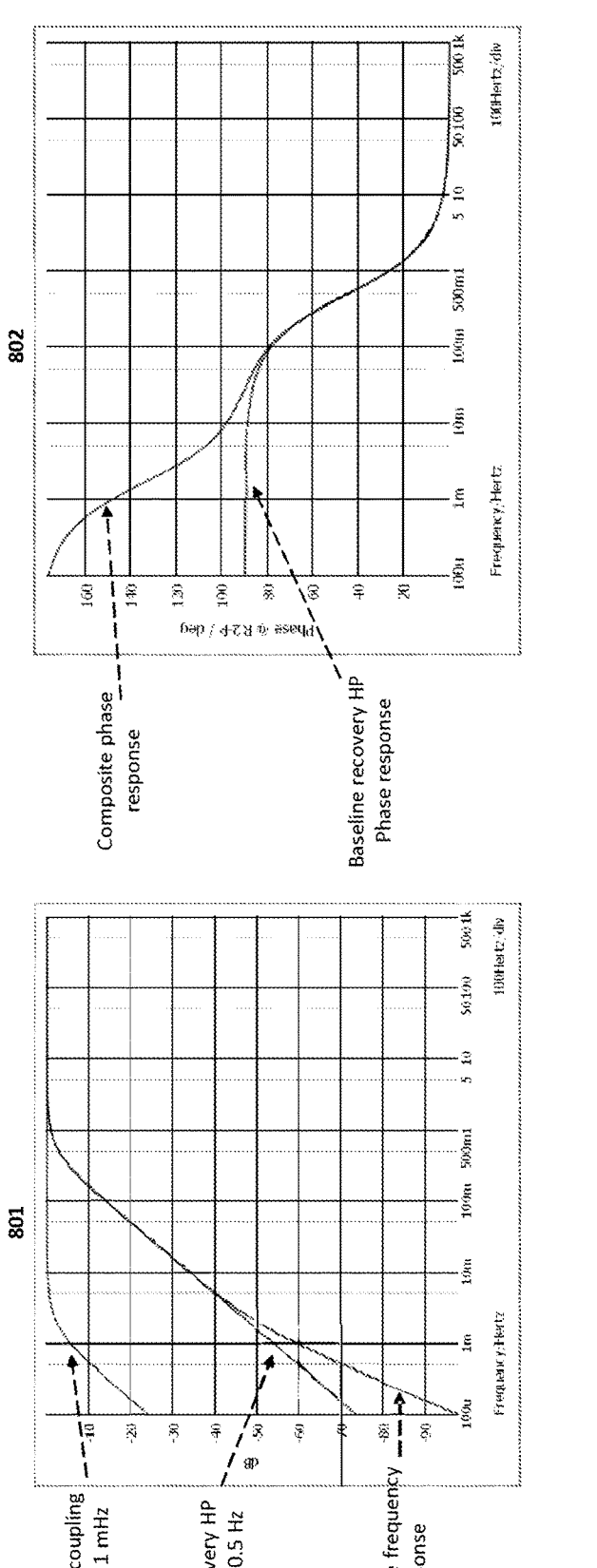
FIGS. 8A and 8B are plots of amplitude and phase response for front-end high-pass filter at 1 mHz and baseline recovery high-pass filter at 0.5 Hz.

In the preferred embodiment, the circuit 700 includes a switching mechanism which enables the AC coupling capacitors 701 to be switched in and out of the circuit. This is indicated by the switches bridging the capacitors 701. This configuration enables the device to change between 2 modes of operation, namely DC current, idle mode, and AC current, active mode. In DC mode the AC coupling capacitors are switched out of the circuit permitting DC current to flow to the electrodes. This mode of operation sets the device to a low power state and enables DC lead-on detection to occur, whereby the device detects when skin/electrode contact has been made to both electrodes. When the AC coupled capacitors are switched in to the circuit the second mode of operation is enabled and ECG signal acquisition can occur. This active mode of operation permits the signal to be acquired while removing the electrode potential offsets, with the aid of a high-pass filter. In this embodiment the input AC coupling capacitor and the amplifier input bias resistor form a high-pass filter 705 at the front end of the circuitry 700. The −3 dB breakpoint, or cut-off frequency, of this high-pass filter needs to be below the lower bandwidth of potential offset frequency, such as approximately 0.5 Hz for use in consumer products (~0.05 Hz for clinical use). The −3 dB point is found using the standard formula, $fc=1/2\pi RC$, as shown by the plot 605 in FIG. 6. To ensure this condition is maintained a high-pass filter 502 is incorporated in to the amplifier stages 402 of the circuit 700. This high-pass filter can aid in removing the long RC time-constant due to the effects of the coupling capacitors in combination with the input bias resistors of the amplifier instrumentation 702. With this implementation the time-constant is less than 10% of the AC coupling circuit. The high-pass filter is an integrator positioned in the feedback path 502 of the circuit for baseline recovery. Incorporating 2 high-pass filters, such as the ones disclosed, results in minimal phase difference at frequencies above 0.1 Hz, as can be seen by the amplitude 801 and phase response 802 plots in FIGS. 8(A) and 8(B), respectively. The high-pass filters in this case are a 1 mHz CR high-pass filter for the front end input 705 and a 0.5 Hz integrator baseline recovery high-pass filter 502 at the back-end 402 of the circuit. In addition, an out-of-range detection system 503 is used for fast baseline recovery, keeping the signal average within the linear range of the instrument.

Figure 9:
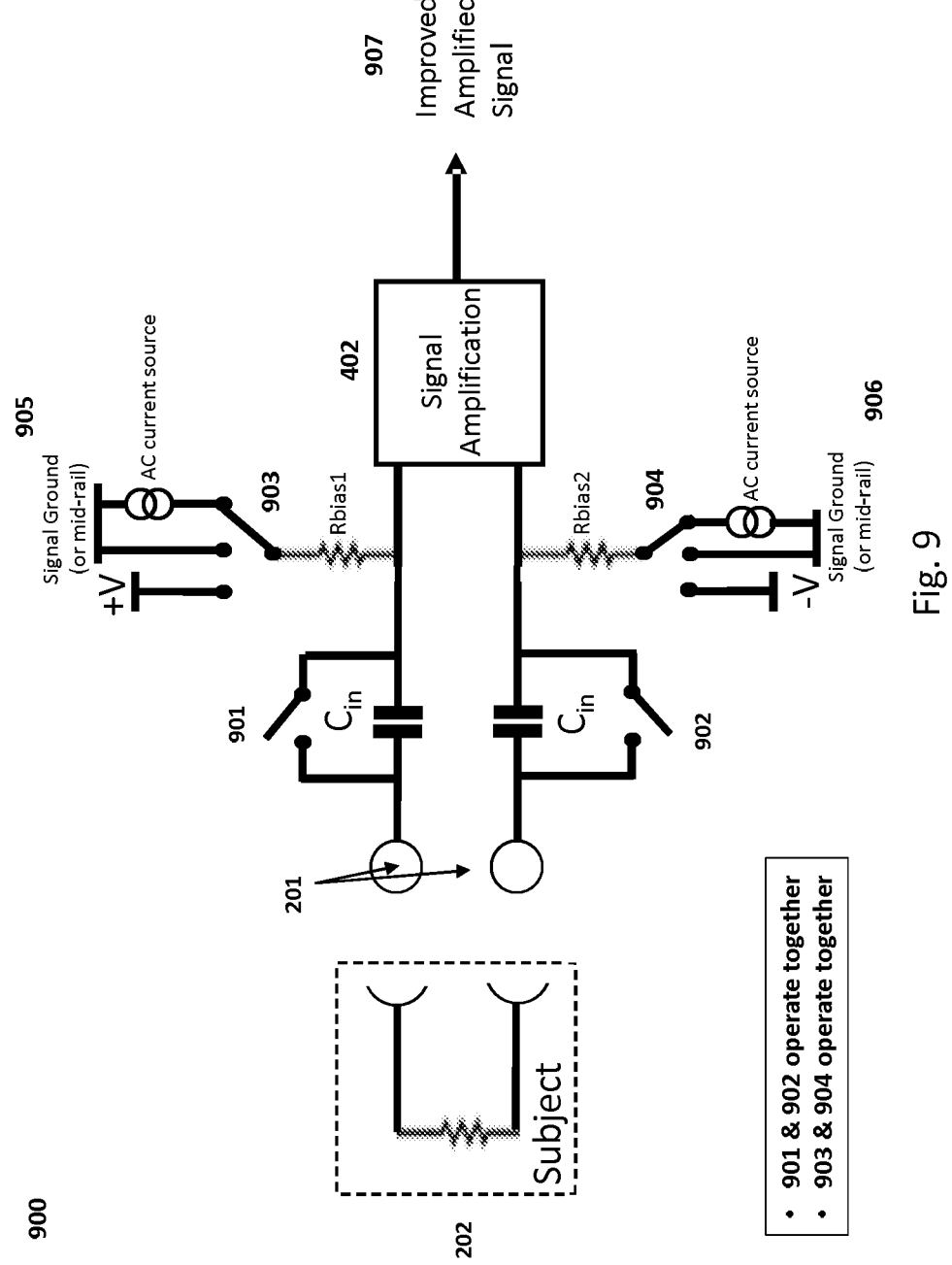
FIG. 9 is a circuit diagram depicting mode switching on front-end components.

In the preferred embodiment, for the switching mechanism to operate a bias switching source 703 is introduced into the circuit 700. The switching can be activated by either using fixed resistors or a programmable constant current source. In a further configuration a mid-rail bias point is introduced with mode switching occurring both across the AC coupling capacitors 901/902 and at the AC current source 903/904 as illustrated in the circuit 900 in FIG. 9. When switching between modes of operation, the pair of capacitor switches 901 and 902 operate together, and the pair of voltage bias switches 903 and 904 operate together. The sequence in which the detection, switching and acquisition is important.

Figure 10A:
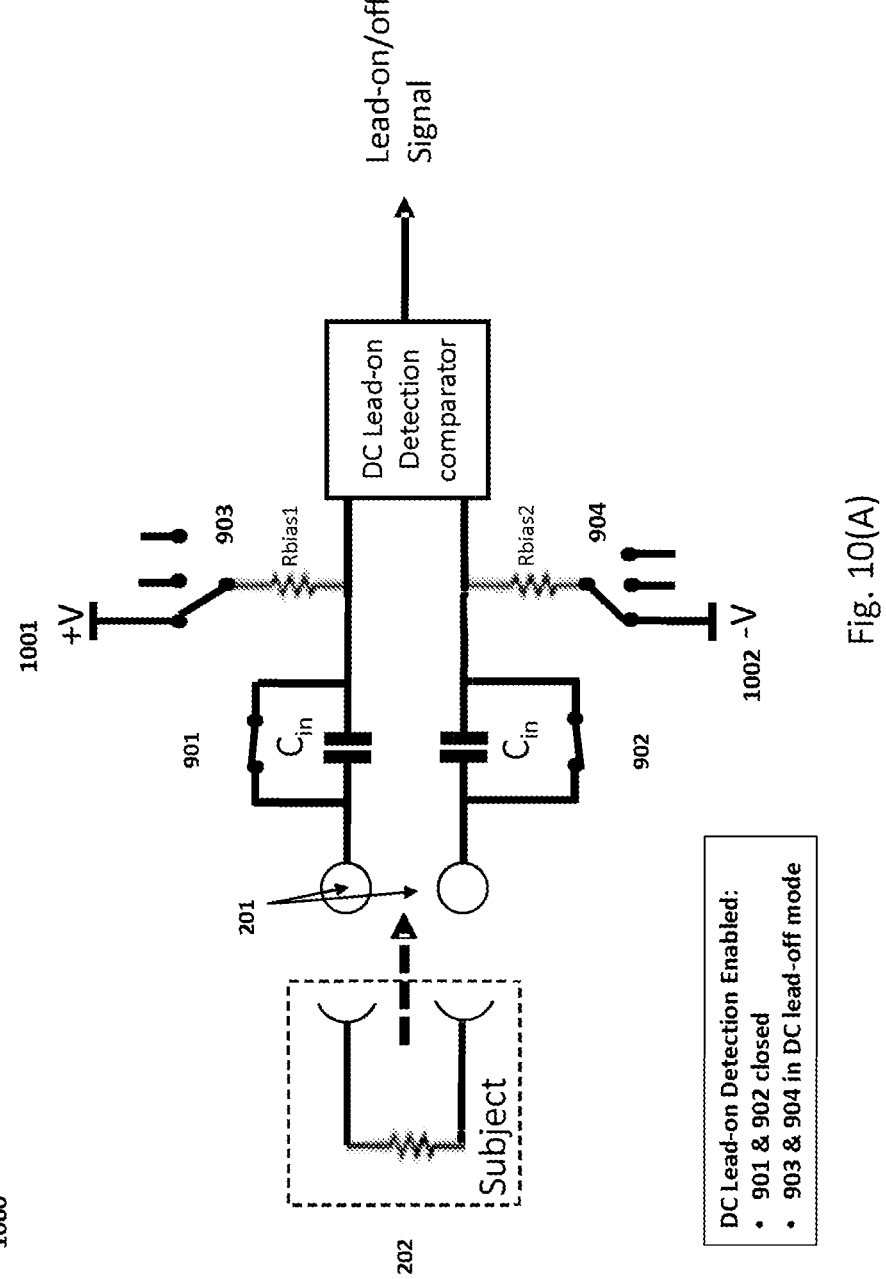
FIGS. 10(A)-(C) are of circuit diagrams showing the mode switching sequence, where (A) is idle mode, waiting for a user to connect, (B) is intermediate mode, discharging electrode and AC-coupling capacitors, and (C) acquisition mode, displaying signal and looking for lead-off via AC detection.
Figure 10B:
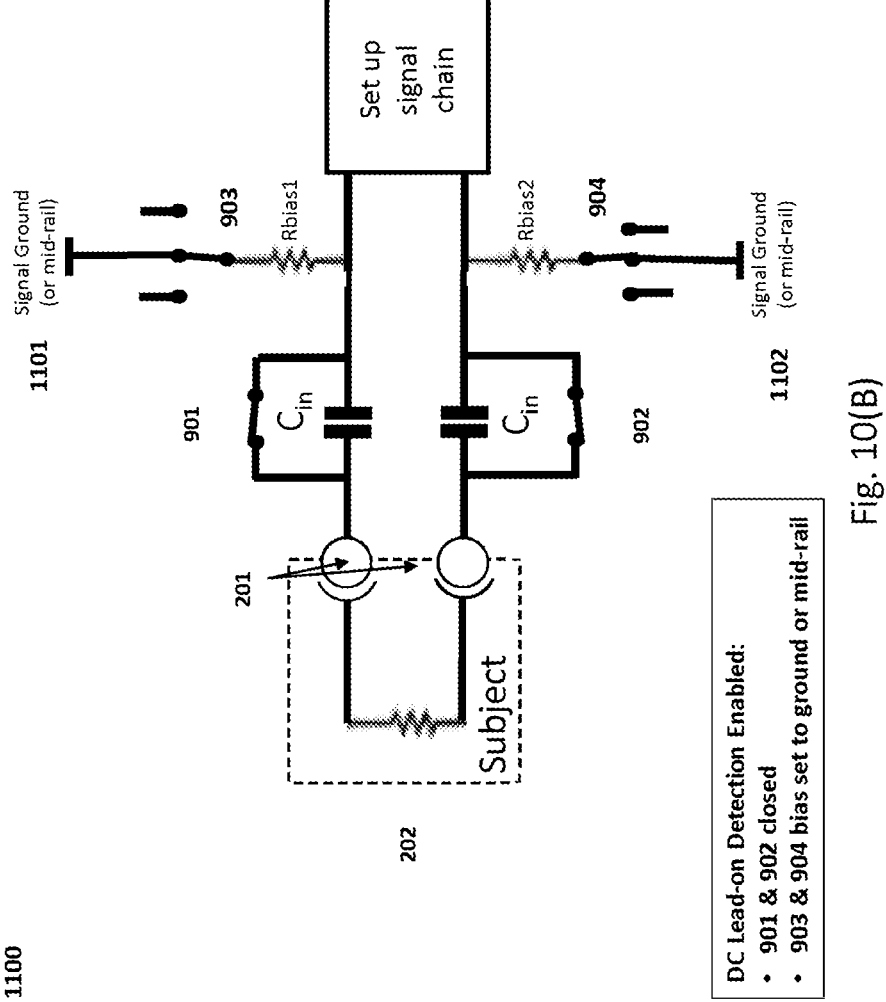
Figure 10C:
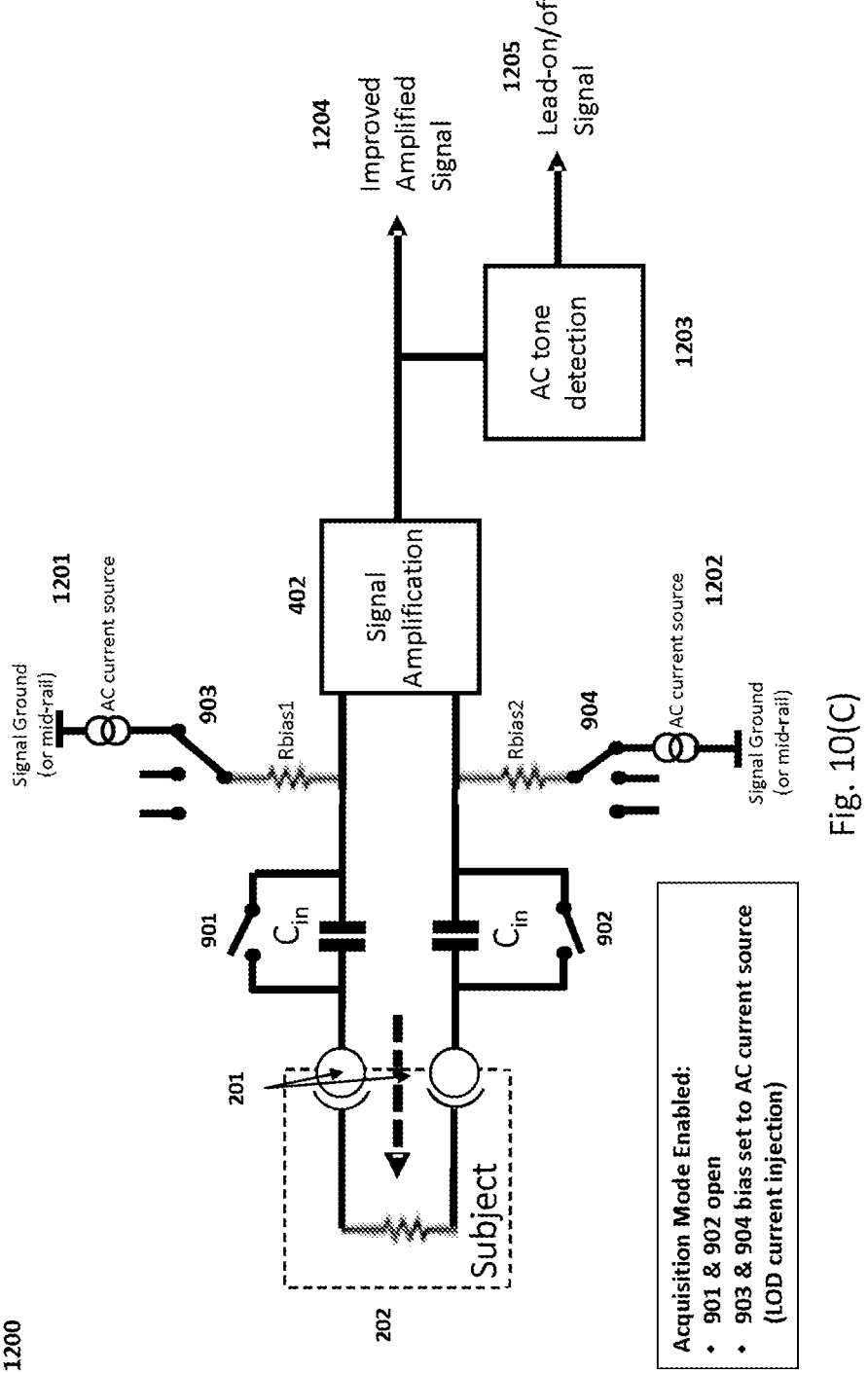

The preferred switching method, from detection to ECG acquisition, is depicted by the switching sequence illustrated in FIGS. 10(A)-(C). Starting in lead-on detection mode 1000, where no skin to electrode 201 contact is made, the circuit is in idle mode with DC current flowing (see FIG. 10(A)). The switches 901 and 902 are enabled to create a short across the AC coupling capacitors, bypassing the current round the capacitors. The bias switches 903/904 (and the voltage comparators 1001/1002) are set to DC voltage permitting the required DC current flow for lead-on detection mode. The circuit will continue to be in this state until contact has been made to the electrodes 201, by a user or subject 202. When skin/electrode contact has been made to both electrodes 201 the comparators 1001/1002 are triggered. Once the comparators 1001/1002 have been validated for a sufficient period of time the biasing termination of both electrodes 201 is performed by switching the biasing switches 903/904 from the active comparator state to mid-rail 1101/1102 for single supply (or ground), removing the bias current supply from the circuit 1100 (see FIG. 10(B)). At this stage, the coupling capacitors are held in a known state, with no charge. Some of the charge imposed by the differential charge on the skin/electrode interface capacitance discharges. This differential charge arises due to the polarisation effects generated at the skin/electrode interface. The discharging occurs as both electrodes 201 are biased to a common voltage 1101/1102. After a sufficient time (usually approximately 0.5 s) the circuit 1200 switches into acquisition mode by switching 903/904 to the AC current source 1201/1202 allowing AC current injection to occur (see FIG. 10(C)). The AC coupling capacitors 901/902 are released and the baseline recovery circuit 1203 is activated, allowing the biopotential ECG signal to be acquired and interpreted correctly. This method and device circuitry provides an overall improved amplified signal 1204, having the best conditions for electrode pickup and signal display, with good common-mode rejection ratio (CMRR) at 50 or 60 Hz, while keeping the power consumption and battery drain low. During this mode, zero mean AC current at a modulating frequency well above the instrument bandwidth can be used to determine when electrode/skin contact is terminated, i.e. subject has removed their skin contact from one of the electrodes, creating an open circuit.

The invention claimed is:

1. A device for acquiring biometric electrical signals, comprising:
    a data acquisition module;
    two dry electrodes;
    two capacitors, each on one side connected to one of the dry electrodes; and two bias resistors, each on one side connected to the other side of said capacitors and the same side of the resistors also being connected to a respective input of a differential amplifier and the other side of the bias resistors being connected to a bias switching component,
    the bias switching component comprising:
        a current supply comprising a direct current (DC) supply, an alternating current (AC) supply, and
        a switch mechanism actuatable to switch selectively between the direct current supply and the alternating current supply so that in a first mode of operation, the switching mechanism is configured to connect the DC supply to the bias resistors;
        and in a second mode of operation, the switching mechanism is configured to connect the AC supply to the bias resistors,
    wherein each of the capacitors is bridged by a switch, which is configured to be closed in the first mode and configured to be open in the second mode,
    wherein in the first mode of operation, a direct electrical connection is made between the dry electrodes and the data acquisition module,
    wherein the second mode of operation allows AC coupled biometric data acquisition,
    wherein in the first mode of operation, the voltage difference between the dry electrodes is an open circuit voltage corresponding to no connection between the dry electrodes and a skin of a subject; and
    wherein the biasing switching component automatically switches to the second mode of operation via the switch when the voltage difference between the dry electrode meets a threshold which corresponds to a connection between the dry electrodes and the skin of the subject to begin detection of biometric electrical signals via the data acquisition module.

2. The device according to claim 1 adapted to switch between the first and the second mode of operation, at an instigation of a user via a user actuatable mode switch.

3. The device according to claim 1 further comprising a battery power source.

4. The device according to claim 1 wherein the dry electrodes comprise or have surface coating comprising:
    chromium-plated metal or plastic;
    coloured or colourable nitrides;
    stainless steels.

5. The device according to claim 1 further comprising one or more of:
    a data storage module to store acquired data and/or library data against which acquired data may be compared for identification of a subject;
    a data comparator module to compare acquired data to stored library data.

6. The device according to claim 1 further comprising a data transmission module to transmit data to a remote recipient, to enable further processing of the data.

7. The device according to claim 1 wherein each dry electrode is provided with:
    a capacitive coupling to couple the dry electrode to the current supply;
    and a direct coupling in parallel to the capacitive coupling which is further provided with a selectively closable switch.

8. The device according to claim 7 wherein the capacitive coupling of each dry electrode comprises an AC-coupling capacitor.

9. The device according to claim 1 wherein the switch mechanism further comprises a mid-rail bias point, whereby the DC source and the AC source can be selectively switched in and out of the circuit via the mid-rail bias point.

10. A system for acquiring biometric electrical signals, comprising:
  a device according to claim 1,
  an additional receiving device,
  a wireless communication system operable to effect communication of data between the device and the additional receiving device,
  a data storage module comprising a part of the device and/or the additional receiving device.

11. The system according to claim 10 wherein the data storage module comprises stored library data.

12. The system according to claim 10 further comprising a data comparator module to compare acquired data to stored library data, for identification identification/authentication purposes, or longer term biometric monitoring.

13. A method for acquiring biometric electrical signals comprising:
  providing a device having:
    two dry electrodes;
    two capacitors, each on one side connected to one of the dry electrodes; and
    two bias resistors, each on one side connected to the other side of said capacitors and the same side of the resistors also being connected to a respective input of a differential amplifier and the other side of the bias resistors being connected to a bias switching component,
    the bias switching component comprising:
      a current supply comprising a direct current (DC) supply, and an alternating current (AC) supply; and
      a switch mechanism actuatable to switch selectively between the direct current supply and the alternating current supply so that:
        in a first mode of operation, the switching mechanism is configured to connect the DC supply to the bias resistors; and
        in a second mode of operation, the switching mechanism is configured to connect the AC supply to the bias resistors, wherein each of the capacitors is bridged by a switch, which is configured to be closed in the first mode and configured to be open in the second mode,
      whereby the device is selectively switchable between:
        a first mode of operation, wherein the DC current supply and the DC connection are selected, and a direct current is supplied to each dry electrode; and
        a second mode of operation, wherein the AC current supply and the capacitive coupling are selected and an alternating current is supplied to each dry electrode;
          wherein, in the first mode of operation, the voltage difference between the dry electrodes is an open circuit voltage corresponding to no connection between the dry electrodes and a skin of a subject; and
          wherein the biasing switching component automatically switches to the second mode of operation via the switch when the voltage difference between the dry electrode meets a threshold which corresponds to a connection between the dry electrodes and the skin of the subject to begin detection of biometric electrical signals via the data acquisition module;
  operating the device in the first mode when the dry electrodes are not in contact with a subject;
  operating the device in the second mode when the dry electrodes are in contact with the skin surface of the body of a subject; and
  acquiring biometric electrical signals when the device is operating in the second mode.

14. The method according to claim 13 wherein the device switches between the first mode of operation and the second mode of operation is via a mid-rail or ground.

15. The method according to claim 13 wherein the acquired biometric electrical signal data is compared to older template signal traces.

16. The method according to claim 13, wherein the acquired biometric electrical signal data is transmitted to a remote recipient via wireless communication, following the acquisition of such data, allowing for further processing of the data.

* * * * *